United States Patent [19]

Kawai et al.

[11] Patent Number: 4,950,258
[45] Date of Patent: Aug. 21, 1990

[54] PLASTIC MOLDED ARTICLES WITH SHAPE MEMORY PROPERTY

[75] Inventors: Tatsuya Kawai; Takashi Matsuda, both of Hiroshima, Japan

[73] Assignee: Japan Medical Supply Co., Ltd., Hiroshima, Japan

[21] Appl. No.: 301,501

[22] Filed: Jan. 25, 1989

[30] Foreign Application Priority Data

Jan. 28, 1988 [JP] Japan .................................. 63-17574

[51] Int. Cl.⁵ ............................................. A61M 25/00
[52] U.S. Cl. ................................... 604/281; 264/230; 264/DIG. 40; 264/DIG. 41
[58] Field of Search ............................ 604/281, 282, 8; 264/230, DIG. 40, DIG. 41; 128/325, 334 R, 335, 335.5, 336

[56] References Cited

U.S. PATENT DOCUMENTS 3,797,499  3/1974  Schneider .
4,523,591  6/1985  Kaplan et al. .
4,603,595  8/1986  Ikada .
4,874,360  10/1989  Goldberg et al. ................ 604/281

FOREIGN PATENT DOCUMENTS 89859   6/1982  Japan .
163309  10/1982 Japan .
53528   3/1984  Japan .
220648  9/1986  Japan .
82976   4/1987  Japan .

Primary Examiner—John D. Yasko
Attorney, Agent, or Firm—Kramer, Brufsky & Cifelli

[57] ABSTRACT

Plastic molded articles having characteristic properties of both shape-memory and biodegradability and a process for preparing the same are disclosed. The molded products consist of homopolymers of lactide or glycolide or copolymers of lactide and glycolide. The molded articles of this invention are particularly useful for a variety of medical devices.

12 Claims, 4 Drawing Sheets

PLASTIC MOLDED ARTICLES WITH SHAPE MEMORY PROPERTY

FIELD OF THE INVENTION

This invention relates to plastic molded articles with a shape-memory property. More particularly this invention relates to shape-memory molded articles consisting of essentially homopolymers or copolymers of lactide or glycolide and also relates to applications thereof.

BACKGROUND OF THE INVENTION

A variety of metallic alloys which exhibit a shape-memory property are known in the art. Examples of such metallic alloys include Ti-Ni, Ni-Al, Ag-Cd, Au-Cd and the like. Of these alloys, Ti-Ni alloy, exhibiting good mechanical properties and chemical stability, has been investigated for its medical applications as a biocompatible functional material. The applications for this metallic alloy include staples for joining bone and for hollow organ anastomosis, wherein the metallic alloy product is capable of recovering a memorized shape on heating by the body temperature and of retaining a constantly stable strength. A device for preventing blood vessel obstruction is disclosed in Japanese Patent Application (Laid-Open) No. 89859/1982; a medical capsule is disclosed in No. 163309/1982; a blood vessel expander is disclosed in No. 82976/1987, and an artificial blood vessel with rings is disclosed in No. 220648/1987. Furthermore, an application for a clip for cerebral aneurysm has been proposed.

In addition to the metallic alloys, it is also known that certain polymeric materials exhibit the property of shape memory. As for polymers with a shape-memory property, an invention related to norbornene polymers is disclosed in Japanese Patent Application (Laid-Open) No. 53528/1984 (corresponding to European Patent No. 105,775.)

One of the major problems associated with the prior art shape memory metallic alloys and polymers, at least in terms of their use in medical applications, is that they are nonbiodegradable. Therefore, the products formed from the shaped molded materials remain in the patient's body, even after the desired results have been achieved. Often, a second operation or other medical procedure is needed to remove the used materials, exposing the patient to increased risks of complication and adding to the cost of the overall procedure.

Accordingly, it is one object of the present invention to provide polymeric materials which exhibit a shape memory property and are also biodegradable.

Another object of the present invention is to provide molded products formed from the shape memory polymers of the present invention which are useful in medical applications.

These and other objects and advantages of the present invention will become apparent from the following specification.

SUMMARY OF THE INVENTION

This invention provides molded articles formed from polymers which are biodegradable and exhibit a shape-memory property and also provides a variety of medical devices utilizing such molded articles. The molded articles of this invention consist essentially of homopolymers of lactide or glycolide or copolymers thereof, and have their shape fixed by a deformation treatment after being molded to a desired shape.

Medical devices made of homopolymers of lactide or glycolide or copolymers of lactide and glycolide are disclosed in, interalia, U.S. Pats., Nos. 3,797,499, 4,523,591, and 4,603,695 and the biodegradability of these materials is already known. However, there had heretofore been no description of their shape-memory property. The present invention is based on the new discovery that the molded articles formed from homopolymers of lactide or glycolide, or copolymers thereof exhibit a shape memory effect.

Shape-memory molded articles of this invention are obtained by molding the aforementioned polymers into a desired shape, memorizing the shape by heating the polymers and keeping them at a prescribed temperature, if necessary, deforming the products to another shape by heat-softening to an extent to make deformation possible, and then cooling the products to fix them in the deformed state. The shape memory molded articles of this invention can be used for tissue suture devices, devices to prevent blood vessel obstruction, blood vessel expanders, cerebral aneurysm clips, medical capsule devices, artificial blood vessels with rings, hemostatic clips and the like.

The shape-memory molded articles of this invention, having once memorized a shape, can recover exactly or approximately the initially memorized shape upon heating again, even after being deformed at a temperature lower than that for the shape memorizing. In addition, the shape memory molded articles of this invention, consisting essentially of homopolymers or copolymers of lactide or glycolide, are absorbed by the patient's body after a certain period of time, making subsequent removal unnecessary.

BRIEF DESCRIPTION OF THE DRAWINGS

Examples of various types of medical devices that utilize the shape-memory molded articles of this invention are illustrated by the drawings.

DETAILED DESCRIPTION OF THE INVENTION

Figure 1A:
FIG. 1 is the frontal view of a staple for tissue suturing.

The shape-memory molded articles of this invention consist essentially of homopolymers of lactide or glycolide or copolymers of lactide an glycolide. When copolymers of lactide and glycolide are used to form the molded products, the copolymers preferably consist essentially of a composition of 90–10 mol.% lactide and 10–90 mol% glycolide, and most preferably consist essentially of 80–20 mol.% lactide and 20–80 mol% of glycolide. Within these specified ranges, the copolymers exhibit desirable deformation characteristics. For example, the copolymers are more pliable and readily deformable at lower temperatures when their mole ratio of lactide and glycolide approximates to 1:1.

In addition, the shape-memory molded articles may additionally include additives such as coloring agents, stabilizers, fillers and the like, in an amount such as will not alter the desired shape-memory and biodegradability properties of the molded articles.

The homopolymers or copolymers of lactide or glycolide of this invention can be prepared in accordance with the processes described in, for example, Japanese Patent Publication No. 7796/1967 (corresponding to British Patent No. 1,040,168), Japanese Patent Publication No. 13595/1970 (corresponding to U.S. Pat. No. 3,442,871), and Japanese Patent Publication No. 14688/1981 (corresponding to U.S. Pat. No. 3,839,297). The polymers of this invention exhibiting the shape-memory property should exhibit a molecular weight in the range of 1,000–1,000,000 and preferably should have a molecular weight above 10,000, in order to achieve good mechanical strength.

In the production of the molded articles of this invention, a molded article with the shape to be memorized is prepared first. Plastic molding methods well known to those in the art can be used to form the articles of the present invention. Examples of molding techniques include melt molding, solution molding and the like. Injection molding extrusion molding, compression molding and other methods can also be used as the melt molding technique. In one solution molding technique, the polymer is dissolved in a solvent, formed into the desired shape, and then coagulated by contact with a coagulating substance, such as water or alcohol, which can dissolve the solvent but cannot dissolve the polymer. In another solution molding technique, a polymer solution is given a desired shape and is then solidified by drying the solvent.

The molded articles prepared as above and then deformed retain the memory of their original shape. By heating and maintaining the molded articles in a deformed state at a prescribed temperature for a prescribed period of time, the newly deformed shape can be memorized. The latter method of memorization is useful in cases where a delicate modification of the memorized shape is needed, for example when production of molded articles, each piece with a different memorized shape, is required; and molding of an intended shape by use of a mold is difficult. Application of the foregoing molding methods makes the shapes that can be memorized by the molded articles of this invention, useful not only for articles such as wires, films bars, and boards, but also for complicated shapes such as coils.

After the molded product with the desired shape is formed, the product is deformed at a deforming temperature. The product is then hardened by cooling. The thus prepared molded articles automatically recover their originally memorized or nearly-so shapes on heating at a prescribed temperature. In addition, after a certain period of time after their application, the molded products are degraded and eventually disappear altogether.

The temperature for deformation treatment of a molded product with a previously memorized shape is one that makes possible ready deformation without producing cracks and does not exceed the temperature adopted for the shape memorization. Deformation treatment at a temperature exceeding that for the original shape memorization will cause the object to memorize a new deformed shape. There are no particular limitations on the manner in which the deformation can be achieved. Deformation can be achieved either by hand or by means of a suitable device selected according to the shape, size, thickness and other desirable characteristics of the molded products. Deformation by heating can be accomplished either by means of heaters of a special design or under an atmosphere of a suitable hot gas or liquid.

Cooling is required for fixation of the deformed shape. The cooling temperature must be one at which the molded products do not cause plastic deformation. Preferably the cooling temperature is 20° C. or below for general cases, although the temperature may differ depending upon the particular polymer employed.

In order to keep the shapes as fixed, the shape-memory molded products of this invention must be stored at a temperature which will not cause plastic deformation of the polymers. Preferably, the shape-molded memory products are stored in a refrigerator. In addition, because homopolymers and copolymers of lactide or glycolide hydrolyze on absorption of water, after drying they should be kept in a container made from a water-vapor nonpermeable material, such as aluminum, as a barrier against water vapor in the air. Another acceptable way of forming a barrier against water vapor is to submerge the molded products in high-purity ethyl alcohol or propyl alcohol.

Releasing a molded product from deformation to recover the originally memorized or nearly-so shape can be achieved by heating. On heating, preferably at a temperature of about 30°–100° C., the deformation is automatically released and the memorized shape recovered. The higher the temperature for heating, the shorter the time for recovery of the originally memorized shape. The means for this heating is not limited. Like the heating for deformation treatment, heating can be accomplished by using a gas or liquid heating medium, heating devices, ultrasonic waves, or the like. Of course, in an application involving a living body, care must be taken to utilize a heating temperature which will not cause burns. When a liquid heating medium is used, physiological saline solution or alcohol is preferable. In addition, in applications involving a living body, heating with body heat is possible. In the latter case, the temperature for shape memorization should be as low as possible. The recovery of the memorized shape occurs fairly slowly.

However, when there is a risk that the shape recovery will begin through a lengthy procedure, higher shape-memory temperature is preferable in order to make the shape recover at a slightly higher temperature than the bodily temperature.

Because the molded articles of the present invention readily recover the originally memorized shapes, they are particularly useful in applications where the mounting, assembling, introduction or other aspects of handling the objects in their initial shapes, are difficult. In use of the molding articles of this invention, a memorized shape is temporarily deformed to make the mounting or assembling of the object easier, and is recovered after the handling. In addition, the molding articles of this invention, having the properties of retaining mechanical strength for a certain period of time and then of decomposing for absorption by the living body, are very useful in medical applications that require disappearance of the molded article after a prescribed period of time.

The time required for the molded article to be completely absorbed by the living body will differ, depending in part on the composition of the polymer, its molecular weight and the contents of the monomers or oligomers. In general, for a homopolymer of glycolide, deterioration and disappearance of the molded product will occur in about one to three months; for a homopolymer of L-lactide or D-lactide, in about one to three years respectively and for a homopolymer of DL lactide, in about three to six months. For copolymers of lactide and glycolide, the period of time until absorption falls between those described above, with the tendency that copolymers with a considerably high mol.% of glycolide show the periods similar to those for homopolymers of glycolide as above, and copolymers with a very high mol.% of lactide show periods close to those for homopolymers of lactide as above.

Referring now to the drawings, several examples of specific applications are explained.

Figure 1B:
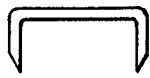

FIG. 1 illustrates an example of a staple for tissue suturing, wherein (a) illustrates a memorized shape, and (b) illustrates a deformed shape. When two tissues to be sutured are brought together, they are pricked with both ends of a staple in the (b) form, and the staple is then heated to recover the (a) form. In this fashion, the tissues are sutured and fixed together. The tips of the staple are preferably sharpened as illustrated in the FIG. 1.

Figure 2:
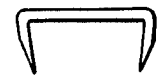
FIG. 2 is a frontal view of another example of a staple for the same purpose.

FIG. 2 shows another example of memorized shape of a staple. A staple with both ends somewhat bent inward from the right angle like this can retain a considerable strength.

Figure 3A:
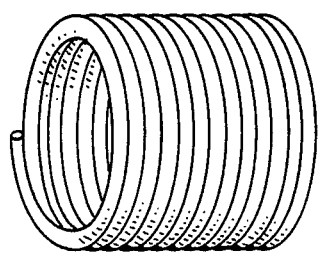
FIGS. 3, 4 and 5 are perspective views of devices for prevention of blood vessel, sometimes referred to as obstruction preventers, or blood vessel expanders.
Figure 3B:
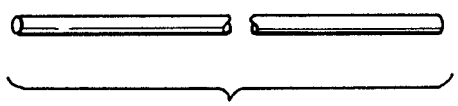

FIG. 3 illustrates a device for prevention of blood vessel obstruction or expansion of a constricted part of a blood vessel. The illustration (a) shows a memorized shape that is coil-shaped. The device with this shape is deformed to a straight bar as shown in (b) or to a coil of a smaller diameter, fixed in the deformed shape, inserted into a blood vessel, and then heated to recover the memorized shape of (a), thus enabling it to prevent blood vessel obstruction or expand the constricted part of a blood vessel. In this example of a coil-like memory shape, it is difficult to obtain the memory shape directly by molding a coil-shaped article. Therefore, the article is first molded into a bar and then formed into a coil by winding the molded bar around a cylinder, heated, with heating maintained for a predetermined time, preferably at a suitable temperature exceeding 40° C., to effect the memorization of the coil shape.

Figure 4A:
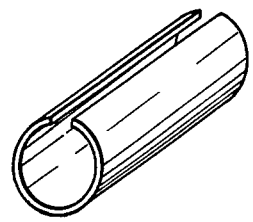
Figure 4B:
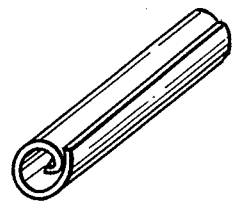
Figure 5A:
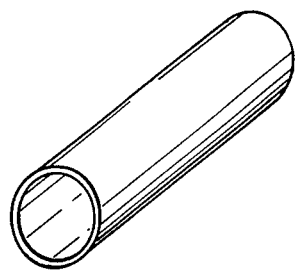
Figure 5B:
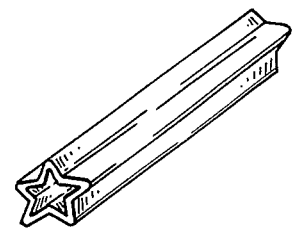

FIG. 4 and FIG. 5 illustrate other examples of devices for preventing blood vessel obstruction or for expanding constricted blood vessels. In both figures, (a) illustrates a memorized shape, and (b) a deformed and fixed shape for insertion into a blood vessel. The device shown in FIG. 4, having a cut through the length of the cylinder, is deformed by circumferential compressing and fixed in the shape. The device shown in FIG. 5, with a simple cylinder shape, is deformed by diametrical compression to form a pleated smaller diameter form and fixed in the shape.

Figure 6A:
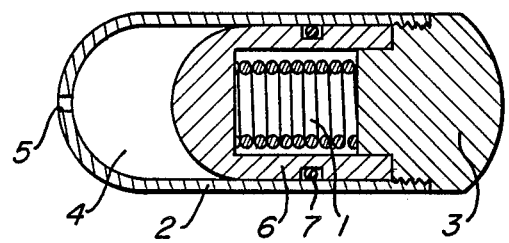
FIG. 6 is the cross-sectional view of a medical capsule device.
Figure 6B:
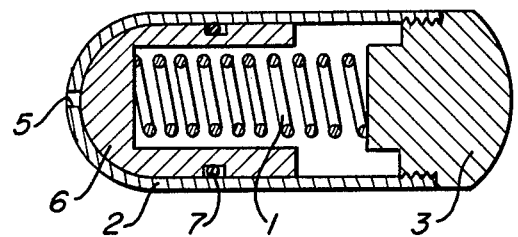

FIG. 6 illustrates a capsule device containing a drug. The device comprises: a capsule proper 2 with a bottom and an opening; a lid 3 attached to the opening of the capsule proper; a movable part 6; and an actuator 1. The movable part 6, having the outer surface with the same shape as the inner surface of the capsule proper 2, can slide back and forth in the capsule proper. When the movable part 6 is positioned at the right side as shown in (a), a drug-containing cavity 4 is formed to contain a prescribed amount of a drug. There is a through hole 5 at the bottom of the capsule proper 2. In this capsule device, the actuator 1 is a shape-memory molded product of this invention, which has the memory of an extended shape as shown in (b) of the figure. The actuator, deformed and fixed to the shrunken form as shown in (a), is assembled into the capsule, and the drug is charged into the drug-containing cavity. The capsule in this condition is taken by a patient or surgically placed in the body. On heating the capsule when necessary, the actuator 1 stretches as shown in (b) pushing the movable part 6 and extrudes the drug through the hole 5, thus effecting administration of the drug to a desired location of the patient's body at a desired timing. Use of a capsule device wholly made of bioabsorbable materials can give rise to the desirable result that the entire capsule automatically degrades after its application.

Figure 7:
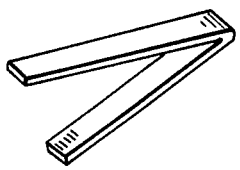
FIG. 7 is a perspective view of a clip for cerebral aneurysm.
Figure 8A:
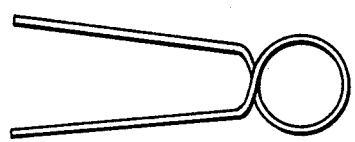
FIG. 8 is a frontal view of another example of a clip for cerebral aneurysm.
Figure 8B:
Figure 8C:
Figure 8D:
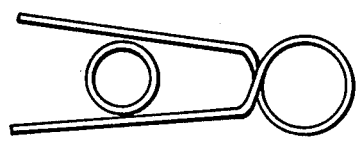

FIG. 7 and FIG. 8 illustrate two examples of cerebral aneurysm clips. An example of a shape to be memorized is shown in FIG. 7, and another example in FIG. 8 (a). The manners for their application are the same in both examples: during a craniotomy, arteries are closed by placing deformed clips on the part of cerebral aneurysm that should be prevented from rupture and then letting the clips recover the closed shape. If the blood vessels or nerves are erroneously clipped together, the original open shape of the clips can be recovered by heating and clippings are made again. FIG. 8 illustrates these procedures. A clip with the memorized shape of (a) is deformed to the opened shape of (b) in which the arms of the clip are in mutually opposite positions. After being placed on the part of cerebral aneurysm, the clip is caused to form a clip of shape (c) to close the artery. When wrong blood vessels or nerves are clipped together or any inadequate clipping is made, heating can cause the clip to recover the shape of (a) by the shape-memory effect so that the clip can be easily freed as shown in (d).

Figure 9:
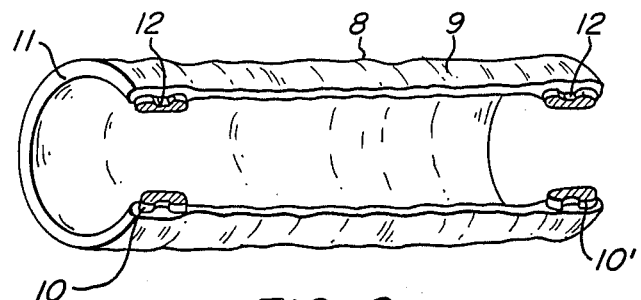
FIG. 9 is a perspective cross-sectional view of an artificial blood vessel with rings.
Figure 10A:
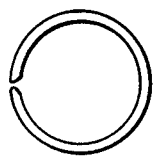
FIGS. 10 and 11 are the frontal views of the rings of the artificial blood vessel illustrated in FIG. 9.
Figure 10B:
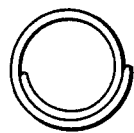
Figure 11:

FIG. 9 illustrates an example of using this invention for the rings to be attached to an artificial blood vessel with rings. An artificial blood vessel with rings consists of an artificial blood vessel proper 9, made of, for example, knitted polyester and other fibers, and rings 10 and 10' attached to both ends of the artificial vessel. Each ring is covered with a ring cover, which, as shown in the drawing for example, has a circumferential groove 12 or 12' in the middle to make possible easier fixation of the ring to a natural blood vessel. This artificial blood vessel with rings is used for the purpose of strengthening a natural blood vessel by its insertion into the inside of a blood vessel part that is in danger of puncture due to cerebral aneurysm or the like. This ring is made as a shape-memory molded product of this invention. As an example of memory shape, either a perfect ring or a partly cutout ring as shown in FIG. 10 (a) may be adequate. In application, the ring is circumferentially compressed to a smaller diameter in the case of FIG. 10; and for a perfect ring, it is diametrically compressed to a smaller diameter as shown in FIG. 11. Thus, owing to the diameter contraction at the ends, insertion of an artificial blood vessel into a natural blood vessel can be made easier than conventional methods. On heating after the insertion into a blood vessel, the rings recover their original larger diameter effecting tight contact with the inner wall of the blood vessel; next, the blood vessel is fastened from outside for fixation at the positions of ring grooves 12 and 12'; and finally the incised part of the blood vessel is closed by suturing.

Figure 12A:
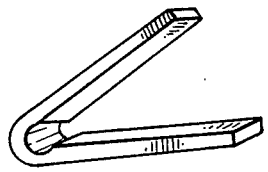
FIG. 12 is the oblique view of a hemostatic clip.
Figure 12B:
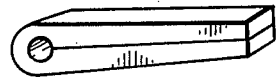

FIG. 12 illustrates an application of this invention for a hemostatic clip. The memorized shape is shown in (b), and its deformed shape in (a). Before its application the clip is in the state of (a). A blood vessel part in question is placed at the opened part of the clip, which on heating closes to the shape as shown in (b) to effect hemostasis.

Examples of various types of medical devices as applications of the shape-memory molded products of this invention have heretofore been explained, however, this invention is by no means limited to the examples discussed herein.

Excellent shape-memory effect of the molded products of this invention will be more specifically explained by the following examples.

EXAMPLE 1

A copolymer (10 g), obtained by polymerization by use of stannous octate as catalyst, and having a composition of 80 mol.% lactide and 20 mol.% glycolide and a molecular weight of about 50,000, was dissolved in 100 cc of chloroform. This solution was cast in a thin layer on a glass plate and dried at a room temperature to form a film of 6 mm width × 12 mm length × 0.04 mm thickness, which was further dried at 60° C. for three days and was subjected to examination of its shape-memory effect. The film was folded over lengthwise in the air at 40° C. or 50° C., and then sufficiently cooled in the air to harden and fix the folded shape. Next the film was immersed in alcohol at 42° C.-60° C., and the change of its shape was observed. As the result, all samples except one recovered the original flat shape in confirmation of the shape-memory effect of the material. The times needed for recovery of the shape at varied temperatures are listed in Table 1.

TABLE 1

| Ethanol Temp. | Time for recovery of memory-shape | |
|---|---|---|
| | Film-Folding Temp. 40° C. | Film-Folding Temp. 50° C. |
| 42° C. | 4 min. 11 sec. | no recovery |
| 46 | 2 00 | 3 min. 24 sec. |
| 51 | 0 57 | 0 58 |
| 55 | 0 03 | 0 06 |
| 58 | 0 02 | 0 04 |
| 60 | 0 01 | 0 02 |

The result shows that the higher the temperature for shape recovery, the quicker the recovery occurs; and the lower the temperature for deformation, the quicker the recovery is attained for the same temperature for shape recovery.

EXAMPLE 2

The same polymer solution as used in Example 1 was cast on a glass plate and dried at room temperature to form a sheet of 5 mm width × 10 mm length × 0.2 mm thickness. The sheet was then folded over lengthwise at a room temperature and was subjected to a treatment to memorize the folded shape, i.e., heating for one hour in a hot air at 40° C., or 80° C. Next the folded sheet was cooled to room temperature, heated again to a softened state, then quickly stretched to flatness, and cooled. The flat sheet thus obtained was immersed in alcohol at 30° C.-70° C., and the times needed for recovery of the memorized folded shape were measured. The results are shown in Table 2.

TABLE 2

| | Time for recovery of memorized shape | | |
|---|---|---|---|
| Ethanol Temp. | Temp. for shape memorization 40° C. | Temp. for shape memorization 60° C. | Temp. for shape memorization 80° C. |
| 30° C. | 0 min. 58 sec. | 4 min. 01 sec. | — |
| 33° C. | 0 14 | 1 39 | — |
| 36° C. | 0 10 | 0 27 | — |
| 37° C. | 0 05 | 0 50 | — |
| 38° C. | 0 06 | 0 13 | — |
| 40° C. | 0 01 | 0 02 | — |
| 50° C. | momentary | 0 04 | 0 min. 54 sec. |
| 58° C. | momentary | momentary | 0 06 |
| 70° C. | momentary | momentary | momentary |

The results demonstrate that the lower the temperature for shape memorization, the quicker the recovery of shape occurs.

EXAMPLE 3

A powder of lactide homopolymer with a molecular weight of about 50,000 was packed in a polytetrafluoroethylene tube 2 mm in inner diameter, melted by heating at 200° C., and upon being dropped into ice water, quickly cooled to solidification. A bar 2 mm in diameter and 40 mm long thus obtained was softened in ethanol at 60° C., deformed into a U-shape, and was sufficiently cooled in air to fix the shape. Later, on immersion in ethanol at 60° C., the straight bar shape was recovered in about five seconds.

EXAMPLE 4

A powder of glycolide hompolymer with a molecular weight of about 20,000 was molded into a bar shape product in the same manner as in Example 3 except adoption of the melting temperature of 260° C. In a similar experiment of shape recovery, the original shape was recovered in about a second.

EXAMPLE 5

A chloroform solution of a homopolymer consisting of 80 mol.% lactide and 20 mol.% glycolide was prepared in the same manner as in Example 1. By immersing a glass bar 2 mm in diameter into this solution and lifting it up, a coating of the solution was formed on the bar and dried at a room temperature. The process of this coating/drying was repeated ten times at 3 hour intervals to form a thick polymer coat on the glass bar. After the final sufficient drying at room temperature, the polymer coat was separated and made into a tube 2 mm in inner diameter, 50 mm long, and 0.5 mm thick. This tube was coiled onto the above glass bar at 60° C., and was allowed to stand for 30 minutes in the air at 60° C. to memorize the coil shape. After having been sufficiently cooled in the air to harden, the tube was heated again to become soft enough, when it was quickly stretched to a straight form and cooled to harden. When this straight tube was immersed in ethanol at 60° C., the memorized coil shape was recovered in about 3 seconds.

EXAMPLE 6

An injection-molded V-shape clip made of a copolymer consisting of 80 mol.% lactide and 20 mol.% glycolide was heated by hot air to a sufficient softness, then the clip was deformed to an opened V-shape and cooled to a room temperature to harden. When it was immersed in ethanol at varied temperatures of 50° C. 70° C., it did not recover the original shape at 50° C. even after a 5 minute standing, but it recovered the original V-shape in 36 sec. at 55° C., in 22 sec. at 60° C., in 8 sec. at 65° C., and in 6 sec. at 70° C.

EXAMPLE 7

The same clip as used in Example 6 was heated by hot air to sufficient softness, then the clip was quickly deformed to an opened V-shape and allowed to stand at 80° C. for 30 minutes to memorize the shape. Later, the clip in the opened shape was cooled to a room temperature, and heated again to a softened state, when it was quickly deformed to the original V-shape and cooled. When it was immersed in ethanol at varied temperatures of 50° C.–70° C.: it did not recover the memorized shape at 50° C. even after a 5 minute standing; but it recovered the memorized opened shape in 1 min. 30 sec. at 55° C., in 25 sec. at 60° C., in 8 sec. at 65° C., and in 6 sec. at 70° C.

As heretofore described, the molded articles of this invention are useful for a variety of medical devices owing to their excellent shape memorizing effect and also to their biodegradability. This invention can be widely modified in the range as described in its concept and claim, and the above examples represent desirable embodiments of this invention. It should be understood that the invention is not limited by these examples.

We claim:

1. A molded article which can be returned to a previously memorized shape, consisting essentially of polymers selected from the group consisting of lactide homopolymers, glycolide homopolymers and copolymers of lactide and glycolide, said polymers having a shape memory property.

2. A molded article according to claim 1, wherein said polymers are copolymers containing 10–90 mol.% lactide and 90–10 mol.% glycolide.

3. A molded article according to claim 1 wherein said polymers are copolymers containing 20–80 mol.% lactide and 80–20 mol.% glycolide.

4. A molded article according to claim 1 wherein the article is a clip for tissue suturing.

5. A molded article according to claim 1, wherein the article is a device for preventing blood vessel obstruction.

6. A molded article according to claim 1, wherein the article is a device for expanding a restricted blood vessel.

7. A molded article according to claim 1, wherein the article is an actuator for releasing a drug from a medical capsule.

8. A molded article according to claim 1, wherein the article is a clip for a cerebral aneurysm.

9. A molded article according to claim 1, wherein the article comprises rings for attachment to the ends of an artificial blood vessel.

10. A molded article according to claim 1, wherein the article is a hemostatic clip.

11. A process for preparing a molded article according to claim 1, comprising the steps of:
   molding a polymer selected from the groups consisting of lactide homopolymers, glycolide homopolymers and copolymers of lactide and glycolide into an article of a desired shape;
   deforming the molded article into another shape by heat-softening; and
   cooling the deformed article to cause the article to harden.

12. A process for preparing a molded article according to claim 1, comprising the steps of:
   molding a polymer selected from the lactide homopolymers, glycolide homopolymers and copolymers of lactide and glycolide into an article of a desired shape;
   heating the article in the desired shape for a prescribed period of time;
   cooling the article;
   deforming the molded article into another shape by heat softening at a temperature lower than said first heating; and
   cooling the deformed article to cause the article to harden.

* * * * *